United States Patent [19]

Deboeck et al.

[11] Patent Number: 5,545,628
[45] Date of Patent: Aug. 13, 1996

[54] PHARMACEUTICAL COMPOSITION CONTAINING FENOFIBRATE

[75] Inventors: Arthur Deboeck; Paul Maes; Phillipe R. Baudier, all of Carolina, Puerto Rico

[73] Assignee: Galephar P.R. Inc., Carolina, Puerto Rico

[21] Appl. No.: 370,883

[22] Filed: Jan. 10, 1995

[51] Int. Cl.⁶ .................................................. A01N 43/04
[52] U.S. Cl. .......................... 514/49; 424/456; 424/463; 424/478; 424/490; 424/492; 424/1.73; D24/100
[58] Field of Search .......................... 514/49; D24/100; 424/1.73, 456, 463, 478, 490, 492

[56] References Cited

U.S. PATENT DOCUMENTS 4,416,877  11/1983  Bentzen et al. .......................... 424/204

Primary Examiner—Nathan M. Nutter
Assistant Examiner—Dve Truong
Attorney, Agent, or Firm—Oblon, Spivak, McClelland, Maier & Neustadt, P.C.

[57] ABSTRACT

A pharmaceutical composition is provided for treating hyperlipidemia or hypercholesterolemia or both in a mammal, which contains an effective amount of each of fenofibrate and an excipient containing one or more polyglycolyzed glycerides.

15 Claims, No Drawings

PHARMACEUTICAL COMPOSITION CONTAINING FENOFIBRATE

BACKGROUND OF THE INVENTION

1. Field of the Invention

The present invention relates to a pharmaceutical dosage form of fenofibrate having enhanced bioavailability, as well as to an advantageous process for making the same.

2. Description of the Background

Fenofibrate or P-(4-chlorobenzoyl)-phenoxy isobutyrate isopropyl ester is useful for the treatment of adult patients with very high elevations of serum triglyceride levels and/or cholesterol levels. The usual daily dosage is 300 mg which is administered in two or three doses. Fenofibrate is absorbed as fenofibric acid which is responsible for the pharmacological activity. Fenofibric acid resulting from the hydrolysis of fenofibrate is extensively bound to plasma albumin. The plasma half-life is about 20 hours. Fenofibric acid is excreted predominantly in the urine, mainly as the glucuronide conjugate, but also as a reduced form of fenofibric acid and its glucuronides.

Fenofibrate, is presently available in a pharmaceutical dosage form consisting of hard gelatin capsules containing fenofibrate, lactose starch and magnesium stearate. After oral administration, during a meal, about 60% of the dose of this conventional form is effectively absorbed and found in the blood as fenofibric acid, the main metabolite responsible for pharmacological activity. (Strolin & A1, Act Pharmacal. Toxicol. 1986; 59 (Suppl. 5); 167).

The first attempt to improve the bioavailability of fenofibrate was performed by Ben-Armor and A1, by solubilizing the fenofibrate in dimethyl isosorbide, a nonaqueous solvent with a miscible wetting agent (Labrafil M1944CS) with HLB of between 3–4. In order to use the product in capsules, colloidal silicon oxide was added to increase the viscosity. The liquid so obtained was placed in hard gelatin capsules which, to be leak proof, were sealed. In vivo studies with this formulation indicate that there was no statistically significant difference in bioavailability between this liquid formulation and the conventional form when the product was given with food.

European Patent Application 0330532 discloses a fenofibrate composition wherein the fenofibrate powder is co-micronized with a solid wetting agent. Sodium lauryl sulfate is described as the solid wetting agent of choice. The co-micronized powder so obtained is mixed with capsule filling excipient such as lactose, starch, polyvinyl pyrollidone and magnesium stearate. A formulation of this composition is actually available on the French market under the trade name Lypantyl 200 M®. A study comparing this formulation (Lypantyl 200 M®) to the conventional form was undertaken and a statistically significant increase in bioavailability was indicated for the former. In particular, it was found that 67 mg of the new form gives the same amount absorbed as does 100 mg of the conventional form. (J. L. Suichard & Al Cun Therapeutic Research Vol. 54, NS, Nov. 1993).

Unfortunately, co-micronization of the active drug fenofibrate with the wetting agent sodium lauryl sulfate, although necessary, is a time consuming and costly operation. Further, an inherent drawback of micronization is that the material obtained must comply with very stringent particle size specifications.

Moreover, the filling of hard gelatin capsules with a micronized powder is a difficult operation, particularly if weight variation homogeneity is considered.

Hence, a need exists for a fenofibrate formulation that avoids the use of co-micronization, while providing a bioavailability comparable to that afforded by the conventional fenofibrate formulation which uses co-micronization.

SUMMARY OF THE INVENTION

Accordingly, it is an object of the present invention to provide a fenofibrate formulation not requiring use of co-micronization which, nevertheless, exhibits a bioavailability comparable to formulations of fenofibrate which do.

It is also an object of the present invention to provide a solid, oral dosage form of a fenofibrate formulation that can be prepared by melting the excipients in which the fenofibrate is soluble and, therefore, does not require any particle size specification.

The above objects and others are provided by a pharmaceutical composition for treating hyperlipidemia in and/or hypercholeslerolemia a mammal, which contains an effective amount of each of fenofibrate and an excipient containing one or more polyglycolized glycerides.

DETAILED DESCRIPTION OF THE PREFERRED EMBODIMENTS

The present invention provides a pharmaceutical formulation for treating hyperlipidemia and/or hypercholesterolemia in a mammal, which contains an effective amount of each of a fenofibrate composition and an excipient which contains one or more polyglycolyzed glycerides, the polyglycolyzed glycerides preferably having an HLB value of at least about 10.

The prevent invention is also particularly advantageous for the production of oral solid dosage forms which can be prepared by melting the excipients in which the fenofibrate is soluble, whereby particle size specifications are not required.

The present invention also relates to the addition of a suspension stabilizer to the molten solution of fenofibrate-polyglycolyzed glycerides. The suspension stabilizer avoids the formation of fenofibrate crystals during the cooling of the filled hard gelatin capsules. Suitable suspension stabilizers which may be used are, for example, cellulose derivatives, such as hydroxypropylcellulose, hydroxypropylmethyl cellulose, methyl cellulose, and hydroxyethylcellulose, povidone, poloxamers, $\alpha$, $\Omega$-hydroxy-poly(oxyethylene) poly(oxypropylene)-poly(oxyethylene)bloc polymers. Other suspension stabilizers equivalent to these stabiliers may, of course, also be used.

The present invention is also particularly advantageous for the production of a pharmaceutical composition in that the hot, homogeneous fenofibrate solution is filled in hard gelatin capsules. This filling process permits the obtention of very precise fenofibrate amounts in each capsule.

The present invention is particularly advantageous as well for the production of the present pharmaceutical composition in that the process for manufacturing the composition requires very few steps such as melting, mixing and filling. This renders the present manufacturing process extremely cost effective when compared to one using co-micronization of powders.

Polyglycolyzed glycerides which may be used in the present invention are generally mixtures of known monoesters, diesters and triesters of glycerols and known monoesters and diesters of polyethylene glycols with a mean relative molecular mass between about 200 and 6000. They may be obtained by partial transesterification of triglycerides with polyethylene glycol or by esterification of glycerol and polyethylene glycol with fatty acids using known reactions. Preferably, the fatty acid component contains 8–22 carbon atoms, particularly 10–18 carbon atoms. Examples of natural vegetable oils which may be used include palm kernel oil and palm oil. However, these are only examples. The polyol suitably has a molecular weight in the range of about 200–6000 and preferably contains polyethylene glycol, although other polyols may be employed, such as polyglycerols or sorbitol. They are available on the market under the trade name Gelucire®.

As noted above, the HLB of the polyglycolized glycerides is preferably at least about 10, and more preferably between about 12 and 15. The melting point of the polyglycolized glycerides may be between about 18° C. and 60° C. However, it is especially desirable to use polyglycolized glycerides having a melting point above 30° C., and preferably above 35° C., since there is no need for sealing the capsule, to assure the leak proofness thereof, when such excipients are used.

Further, two or more polyglycolized glycerides may be mixed in order to adjust both the HLB value and the melting point to a desired value. The HLB value and melting point of the composition may further be adjusted with the addition of components such as polyethylene glycols, polyoxyethylene glycols fatty acid esters, and fatty acid alcohols. In view of the present specification, it is well within the skill of the artisan to mix the polyglycolized glycerides to obtain desired HLB values and melting points.

It has also been discovered that the present composition affords an increased bioavailability of the fenofibrate as compared to conventional formulations.

Although the present inventors do not wish to be bound by any particular theories, one plausible mechanism of operation for the present invention is that upon cooling, the melted mixture of hot fenofibrate-polyglycolized glycerides maintains the fenofibrate in liquid form. When absorbed in the gastrointestinal tract of a patient, the gastrointestinal fluids are able to dissolve the fenofibrate due to the HLB value of the excipient mixture, whereby fenofibrate is readily absorbed.

Generally, the composition of the present invention contains from about 5% to 95% by weight of fenofibrate and from about 95% to 5% by weight of excipient including one or more polyglycolized glycerides. It is preferred, however, if the present composition contains from about 20% to 80% by weight of fenofibrate and from about 80% to 20% by weight of excipient. It is even more preferred, however, if the present composition contains from about 30% to 70% by weight of fenofibrate and from about 70% to 30% by weight of excipient.

In a particularly preferred composition, generally about 45% to 55% by weight of fenofibrate is used and about 55% to 45% by weight of excipient containing the one or more polyglycolyzed glycerides is used.

Generally, the method of the present invention entails adding one or more excipients, including the one or more polyglycolyzed glycerides to containing means and then heating the excipients until all components are melted. Then, fenofibrate is added slowly with continuous stirring until all fenofibrate added is dissolved. Stirring is then continued for about 10 minutes to about 1 hour, and preferably for about 15 minutes to about 30 minutes. Then, containing means for the pharmaceutical composition, such as hard gelatin capsules, are filled with the composition using a liquid filing capsule machine having dosing pumps which are heated to the same temperature as the temperature of the molten pharmaceutical composition. Generally, this temperature is about 55° C. to about 95° C. more typically in the range of about 80° C. to 90° C. Upon cooling to ambient temperature, the capsules are packed in bottles. When capsules of size 3 are used, each capsule so prepared contains 67 mg of fenofibrate.

It is advantageous, however, to use the following protocol. To about 3 parts by weight polyglycolized glyceride excipient having a melting point of 44° C. and an HLB value of 14 molten at 80° C., is added about 2 parts by weight of fenofibrate and about 1 part by weight of hydroxypropyl cellulose. After maintaining the solution under agitation for about 20 additional minutes, hard gelatin capsules are filled therewith.

The present invention will now be further described by reference to certain examples which are provided solely for purposes of illustration and are not intended to be limitative.

| | |
|---|---|
| Fenofibrate | 6.7 kg |
| Gelucire ® 44/14 | 5.0 kg |
| Polyoxamer 407 | 5.0 kg |
| | 16.7 kg |

In a stainless steel container, were introduced 5 kg of Gelucire®44/14 and 5 kg of Poloxamer 407, which were then heated at 85° C. until all components are molten. 6.7 kg of fenofibrate was added slowly while continuously stirring the mixture. When all of the fenofibrate was dissolved agitation was maintained for about twenty minutes. Using a liquid filing capsule machine with dosing pumps heated at 85° C., capsules of size 3 was filled with 167 mg of solution. Upon cooling at room temperature the capsules were packaged in bottles. Each capsule so prepared contained 67 mg of fenofibrate.

PHARMACOKINETICAL STUDY

The composition of Example 1 was compared to conventional form in a pharmacokinetical study with 15 healthy subjects. Each subject received 3 capsules of composition of Example 1 (201 mg of fenofibrate) or 3 capsules of Lypantyl 100® (300 mg of the conventional form). The sessions were separated by a wash out period of 7 days. The medications were taken after a high-fat breakfast. Blood samples were obtained before and at different times up to 72 hours after administration. The plasma concentration of fenofibric acid was determined in all available samples using a conventional HPLC method.

Plasma Fenofibric Acid Concentration (mg.l vs. time (h) After Administration
at 3 Capsules of Example 1 (Total amount of Fenofibrate administered: 201 mg)

| Post-dose time (h) | 1 | 2 | 3 | 4 | 5 | 6 | 8 | 9 | 10 | 11 | 12 | 13 | 14 | 15 | 16 | Mean* | SD |
|---|---|---|---|---|---|---|---|---|---|---|---|---|---|---|---|---|---|
| 0 | BLOQ | BLOQ | BLOQ | BLOQ | BLOQ | BLOQ | BLOQ | BLOQ | BLOQ | BLOQ | BLOQ | BLOQ | BLOQ | BLOQ | BLOQ | 0 | — |
| 1 | BLOQ | 0.34 | 0.42 | 0.25 | 0.52 | 0.81 | 0.29 | BLOQ | 0.32 | BLOQ | 0.99 | BLOQ | BLOQ | 0.81 | 0.75 | 0.21 | 0.30 |
| 2 | 0.36 | 1.06 | 3.87 | 4.31 | 5.10 | 6.00 | 4.66 | 6.46 | 2.56 | 2.51 | 3.83 | 1.09 | 3.84 | 3.03 | 5.62 | 2.89 | 2.19 |
| 3 | 3.31 | 2.70 | 7.52 | 8.12 | 12.80 | 7.68 | 7.50 | 7.27 | 6.55 | 4.46 | 5.35 | 3.22 | 12.68 | 6.73 | 9.61 | 6.43 | 3.37 |
| 4 | 4.06 | 5.49 | 6.02 | 10.87 | 13.56 | 8.27 | 0.42 | 8.93 | 8.16 | 6.49 | 7.42 | 5.23 | 13.93 | 7.17 | 11.08 | 7.85 | 3.33 |
| 5 | 4.06 | 6.61 | 6.61 | 10.84 | 12.65 | 6.99 | 9.64 | 11.70 | 9.65 | 9.75 | 12.16 | 5.46 | 14.41 | 8.53 | 13.70 | 8.73 | 2.99 |
| 6 | 4.32 | 7.17 | 6.42 | 10.68 | 12.34 | 6.32 | 12.19 | 16.75 | 11.64 | 8.89 | 11.41 | 5.76 | 15.68 | 9.95 | 10.72 | 10.32 | 3.71 |
| 7 | 3.82 | 7.60 | 4.28 | 8.50 | 11.75 | 5.68 | 8.93 | 8.45 | 11.43 | 6.80 | 8.79 | 3.74 | 7.60 | 9.06 | 8.70 | 8.12 | 2.71 |
| 8 | 4.74 | 6.83 | 3.71 | 5.28 | 9.61 | 4.27 | 8.12 | 6.19 | 9.97 | 5.00 | 7.00 | 3.57 | 7.41 | 6.42 | 6.49 | 6.76 | 2.05 |
| 9 | 5.61 | 8.07 | 2.36 | 5.66 | 8.08 | 3.49 | 7.05 | 4.70 | 7.78 | 6.37 | 6.25 | 6.25 | 3.75 | 4.83 | 5.74 | 5.74 | 1.73 |
| 12 | 2.57 | 3.56 | 0.85 | 2.48 | 4.78 | 1.39 | 2.51 | 1.83 | 3.48 | 2.19 | 2.32 | 2.30 | 3.67 | 2.29 | 2.64 | 2.59 | 0.97 |
| 24 | 1.24 | 1.53 | 0.61 | 1.64 | 3.01 | 0.63 | 1.73 | 1.16 | 2.38 | 1.42 | 1.64 | 1.24 | 1.74 | 1.26 | 1.26 | 1.50 | 0.61 |
| 36 | 0.80 | 0.76 | 0.27 | 0.98 | 2.13 | 0.29 | 1.05 | 0.95 | 1.54 | 1.06 | 1.10 | 0.63 | 1.33 | 0.73 | 0.88 | 0.97 | 0.47 |
| 48 | 0.55 | 0.70 | BLOQ | 0.64 | 1.43 | 0.28 | 0.73 | 0.43 | 0.88 | 0.73 | 0.92 | 0.28 | 0.78 | 0.48 | 0.70 | 0.64 | 0.33 |
| 60 | 0.40 | 0.52 | BLOQ | 0.50 | 1.21 | BLOQ | BLOQ | 0.38 | 0.68 | 0.51 | 0.53 | BLOQ | 0.62 | BLOQ | 0.39 | 0.38 | 0.34 |

Plasma Fenofibric Acid Concentration (mg.l vs time (h) After Administration
at 3 Capsules of the Conventional Form (Total amount of Fenofibrate administered: 300 mg)

| Post-dose time (h) | 1 | 2 | 3 | 4 | 5 | 6 | 8 | 9 | 10 | 11 | 12 | 13 | 14 | 15 | 16 |
|---|---|---|---|---|---|---|---|---|---|---|---|---|---|---|---|
| 0 | BLOQ | BLOQ | BLOQ | BLOQ | BLOQ | BLOQ | BLOQ | BLOQ | BLOQ | BLOQ | BLOQ | BLOQ | BLOQ | BLOQ | BLOQ |
| 1 | BLOQ | BLOQ | BLOQ | 0.25 | BLOQ | BLOQ | 1.90 | BLOQ | BLOQ | BLOQ | 0.63 | BLOQ | BLOQ | BLOQ | BLOQ |
| 2 | BLOQ | 0.99 | 0.25 | 4.67 | 0.34 | 1.52 | 5.83 | 2.45 | 1.53 | 0.42 | 1.55 | 1.03 | 1.40 | 0.47 | 1.28 |
| 3 | 1.75 | 4.62 | 2.16 | 7.39 | 4.51 | 3.72 | 5.89 | 5.12 | 6.54 | 1.71 | 3.58 | 3.47 | 4.75 | 1.48 | 3.79 |
| 4 | 3.25 | 10.24 | 5.57 | 9.13 | 8.83 | 5.00 | 5.76 | 11.97 | 12.91 | 4.37 | 6.94 | 4.22 | 6.40 | 3.55 | 5.08 |
| 5 | 4.53 | 17.36 | 12.20 | 12.16 | 10.43 | 4.77 | 6.57 | 14.17 | 18.00 | 4.93 | 11.45 | 4.30 | 11.12 | 10.65 | 11.35 |
| 6 | 8.77 | 11.92 | 12.93 | 12.08 | 13.18 | 5.66 | 6.62 | 12.31 | 14.42 | 9.03 | 10.58 | 4.17 | 13.21 | 10.11 | 17.47 |
| 7 | 4.75 | 8.21 | 12.12 | 10.71 | 11.36 | 4.84 | 5.90 | 7.33 | 10.86 | 8.08 | 8.25 | 6.34 | 10.22 | 7.21 | 16.35 |
| 8 | 3.64 | 7.03 | 9.29 | 8.39 | 9.62 | 6.34 | 5.80 | 6.67 | 7.50 | 6.37 | 7.09 | 12.05 | 9.16 | 5.74 | 11.79 |
| 9 | 4.24 | 3.43 | 6.20 | 6.90 | 7.96 | 8.66 | 5.30 | 2.61 | 2.85 | 5.11 | 2.85 | 6.53 | 4.92 | 2.29 | 8.06 |
| 12 | 2.36 | 2.03 | 1.88 | 3.12 | 4.76 | 2.53 | 2.19 | 1.14 | 1.73 | 2.66 | 1.38 | 3.31 | 2.31 | 1.33 | 3.08 |
| 24 | 1.17 | 1.17 | 0.92 | 1.56 | 3.27 | 0.95 | 1.47 | 0.94 | 0.90 | 1.48 | 0.92 | 1.72 | 1.39 | 0.81 | 1.69 |
| 36 | 0.70 | 0.50 | 0.61 | 1.02 | 2.06 | 0.49 | 0.71 | 0.71 | 0.58 | 1.07 | 0.55 | 0.81 | 1.13 | 0.54 | 1.03 |
| 48 | 0.49 | 0.50 | 0.43 | 0.66 | 1.77 | 0.31 | 0.74 | 0.81 | 0.34 | 0.69 | 0.40 | BLOQ | 0.83 | 0.54 | 0.74 |
| 60 | BLOQ | BLOQ | 0.30 | 0.49 | 1.48 | BLOQ | 0.49 | 0.54 |  | 0.52 |  |  |  | 0.35 | 0.40 |

The bioavailability, as measured by the extent of absorption (AUC) indicates, that 3 capsules of Example 1 of the present invention (201 mg of fenofibrate AUC=195) are bioequivalent to 3 capsules of the conventional form (300 mg of fenofibrate AUC=221).

That is, the bioavailability of fenofibrate from the composition of Example 1 of the present invention is 1.5 times higher than the bioavailability of fenofibrate of the conventional form.

| | |
|---|---|
| Fenofibrate | 5 kg |
| Gelucire ® 44/14 | 7.5 kg |
| Carbowax 20,000 | 1.5 kg |
| Hydroxypropylcellulose | 2.5 kg |
| | 16.5 kg |

To a heated kettel, 7.5 kg of Gelucire® 44/14 and 1.5 kg of carbowax 20,000 were added and then heated at 85° C. until all components are molten. 5 kg of fenofibrate was added slowly while continuously stirring. When all the fenofibrate was dissolved, 2.5 kg of hydroxypropylcellulose was added and agitation was maintained for about twenty minutes. Using a liquid filing capsule machine with dosing pumps heated at 85° C., capsules of size 0 were filled with 660 mg of solution. Upon cooling at room temperature the capsules were packaged in bottles. Each capsule so prepared contained 200 mg of fenofibrate. 12,701 capsules were produced and individually weighed. Results of the capsule weighing is shown in Table 3.

TABLE 3

| Capsules Weight Variations From 12,701 Capsules | |
|---|---|
| Theoretical Weight | 764.5 mg |
| Mean weight of acceptable capsules (95–105%) | 763.9 mg |
| Standard Deviation of Accepted Capsules | 6.9 mg |
| Relative Standard Deviation of Accepted Capsules | 0.9% |
| Percent of Rejected Capsules (below 95% of Theoretical Amount) | 0.307% |
| Percent of Rejected Capsules (above 105% of Theoretical Amount) | 0.039% |

It may readily be appreciated from Table 3 that the filling process of the present invention is extremely accurate.

PHARMACOKINETICAL STUDY

The composition of Example 2 of the present invention was compared during a Pharmacokinetical study to the co-micronized formulation available on the French market (Lypanthyl 200 M®).

The study was conducted as a single dose, randomized, four-way cross over study in 8 healthy subjects. The subjects were randomly assigned to one of four administration sequences. On each of the four sessions, separated by wash-out periods of 7 days, the subjects received either 200 mg of fenofibrate under the form Lypantyl 200 M® or 200 mg of fenofibrate under the form of Example 2 with and without a high-fat breakfast. Blood samples were taken before and at different times up to 72 hours after administration. The plasma concentrations of fenofibric acid was determined in the samples using on HPLC Method.

The pharmacokinetics parameters obtained are shown in Table 4.

TABLE 4

Pharmacokinetical Parameters After Administration of Lypantyl 200 M ® and Composition of Example 2 Taken With and Without a high Fat Breakfast (Dose 200 mg of Fenofibrate)

| | Without Food | | With Food | |
|---|---|---|---|---|
| | Example 2 | Lipanthyl 200 M ® | Example 2 | Lypanthyl 200 M ® |
| $AUC_{0-72}$ | 107.0 | 101.0 | 181.0 | 184.7 |
| $C_{max}$ | 5.1 | 5.9 | 11.1 | 10.9 |
| $\tau_{max}$ | 5.9 | 5.2 | 5.2 | 5.7 |

The present composition may thus be advantageously used to treat hyperlipidemia and/or hypercholesterolemia in humans. Generally, the effective daily amount of fenofibrate from humans ranges from about 100 mg to 600 mg per day, and preferably from about 100 to 300 mg per day, with the precise amount being determined by the attending physician, considering such parameters as condition severity and body weight, for example.

Having fully described the present invention, it will be apparent to one of ordinary skill in the art that many changes and modification may be made to the above-described embodiments without departing from the spirit and scope of the present invention.

What is claimed as new and desired to be secured by Letters Patent of the United States is:

1. A pharmaceutical composition for treating hyperlipidemia or hypercholesterolemia or both in a mammal, which comprises an effective amount of each of fenofibrate and an excipient comprising one or more polyglycolyzed glycerides.

2. The composition of claim 1, wherein said fenofibrate is present in an amount of 5% to 95% by weight based on the total weight of the composition.

3. The composition of claim 1, wherein the polyglycolyzed glycerides have a HLB value of at least 10.

4. The composition of claim 3, wherein the polylglycolyzed glycerides have a HLB value of from 12 to 15.

5. The composition of claim 1, which further comprises polyalkylene glycols to adjust the HLB value or melting point or both to the desired value.

6. The composition of claim 1, wherein a suspension stabilizer is added.

7. The composition of claim 6, wherein said suspension stabilizer is selected from the group and consisting of cellulose, povidone, poloxamers, α, Ω-hydroxy-poly(oxyethylene) poly(oxypropylene)-poly(oxyethylene)bloc polymers.

8. The composition of claim 1, in which said fenofibrate and said excipient are in unit dosage form and are contained in a hard gelatin capsule.

9. The composition of claim 8, wherein said hard gelatin capsule contains from about 67 mg to about 200 mg of fenofibrate.

10. A method of making a solid oral dosage form of a pharmaceutical composition, comprising an effective amount of each of fenofibrate and an excipient comprising one or more polyglycolyzed glycerides, which method comprises adding said molten fenofibrate and said excipient to hard gelatin capsules, and allowing said said molten fenofibrate and said excipient to cool therein.

11. A method of treating hyperlipidemia or hypercholesterolemia or both in a mammal in need threof, which comprises administering to said mammal an effective amount of a pharmaceutical composition, comprising fenofibrate and an excipient containing one or more polyglycolyzed glycerides.

12. The method of claim 11, wherein said mammal is human, and said effective amount of fenofibrate in said composition is from about 100 mg to 600 mg per day.

13. The method of claim 12, wherein said effective amount of fenofibrate in said composition is from about 100 mg to 300 mg per day.

14. The method of claim 11, wherein said composition is administered orally.

15. The method of claim 10, which is with the proviso that the fenofibrate used is not co-micronized.

* * * * *